United States Patent [19]

Clough et al.

[11] Patent Number: 5,314,892
[45] Date of Patent: May 24, 1994

[54] FUNGICIDAL PYRIMIDINYLOXYPHENYL-3-METHOXY PROPENOATES

[75] Inventors: John M. Clough, Marlow; Christopher R. A. Godfrey, Bracknell; Ian T. Streeting; David P. Bacon, both of Wokingham, all of Great Britain

[73] Assignee: Imperial Chemical Industries PLC, London, England

[21] Appl. No.: 957,232

[22] Filed: Oct. 6, 1992

Related U.S. Application Data

[63] Continuation of Ser. No. 616,454, Nov. 20, 1990, Pat. No. 5,179,098.

[51] Int. Cl.$^5$ .............................. A61K 31/505
[52] U.S. Cl. .................... 514/269; 514/235.8; 514/242; 514/252; 514/273; 514/274; 514/241; 544/123; 544/182; 544/295; 544/296; 544/317; 544/319; 544/321; 544/220
[58] Field of Search ............. 544/300, 315, 317, 319, 544/321, 182, 123, 238, 295, 296; 514/269, 273, 274, 235.8, 242, 252

[56] References Cited

FOREIGN PATENT DOCUMENTS

| | | |
|---|---|---|
| 0178826 | 4/1986 | European Pat. Off. . |
| 0242070 | 3/1987 | European Pat. Off. . |
| 0260794 | 7/1987 | European Pat. Off. . |
| 0242081 | 10/1987 | European Pat. Off. . |
| 0307101 | 8/1988 | European Pat. Off. . |
| 0307103 | 8/1988 | European Pat. Off. . |
| 2935578 | 9/1979 | Fed. Rep. of Germany . |

*Primary Examiner*—Glennon H. Hollrah
*Assistant Examiner*—Brian M. Burn
*Attorney, Agent, or Firm*—William E. Dickheiser

[57] ABSTRACT

Fungicidal compounds having the formula (I):

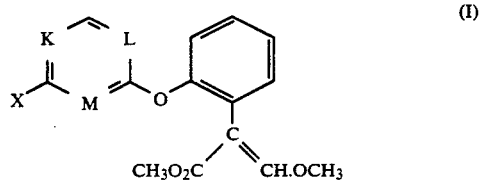

in which any two of K, L and M are nitrogen and the other is CH; and X is an optionally substituted 3- to 6-membered heterocyclic ring containing at least one trivalent nitrogen atom by which it is attached to the central pyrimidine ring.

10 Claims, No Drawings

FUNGICIDAL PYRIMIDINYLOXYPHENYL-3-METHOXY PROPENOATES

This is a continuation of application Ser. No. 07/616,454, filed Nov. 20, 1990, now U.S. Pat. No. 5,179,098.

This invention relates to derivatives of propenoic acid useful as fungicides, to processes for preparing them, to fungicidal compositions containing them, and to methods of using them to combat fungi, especially fungal infections of plants.

According to the present invention there are provided compounds having the formula (I):

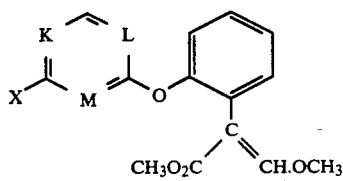

in which any two of K, L and M are nitrogen and the other is CH; and X is an optionally substituted 3- to 6-membered heterocyclic ring containing at least one trivalent nitrogen atom by which it is attached to the central pyrimidine ring.

Because of the unsymmetrically substituted double bond of the propenoate group, the compounds of the invention may be obtained in the form of mixtures of (E)- and (Z)-geometric isomers. However, these mixtures can be separated into individual isomers, and this invention embraces such isomers and mixtures thereof in all proportions including those which consist substantially of the (Z)-isomer and those which consist substantially of the (E)-isomer The (E)-isomer, in which the groups —CO$_2$CH$_3$ and —OCH$_3$ are on opposite sides of the olefinic bond of the propenoate group, are the more fungicidally active and form a preferred embodiment of the invention.

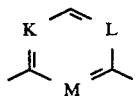

in formula (I) is a pyrimidine ring. Of particular interest is the pyrimidine ring in which K and L are both nitrogen and M is CH.

The group X is an optionally substituted 3- to 6-membered heterocyclic ring containing at least one trivalent nitrogen atom by which it is attached to the central pyrimidine ring. The following are examples of suitable rings: pyrrole, imidazole, pyrazole, 1,2,4-triazole, 1,2,3-triazole, 1,3,4-triazole, pyridone, pyrimidinone, pyrazinone, pyridazinone, 1,2,4-triazinone 1,3,5-triazinone, indole, aziridine, azetidine, pyrrolidine, piperidine and morpholine.

As the nitrogen atom by which X is attached to the central pyrimidine ring is trivalent, X does not include such aromatic nitrogen-containing rings as pyridine, pyrimidine, etc. without modification by, for example, the inclusion of an oxo substituent to form a pyridone or pyrimidone ring.

Thus X is a ring

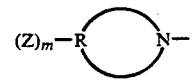

wherein R is a 2- to 5-membered, saturated or unsaturated chain in which the members are carbon atoms and optionally one or more heteroatoms such as nitrogen, oxygen or sulphur; Z is a substituent of the type described below; m is 0 or an integer of from 1 to 5 according to the size and composition of the chain R and as valency allows; and, when m is 2 or more, the substituents Z may be the same or different.

Typically R is a 2- to 5-membered, saturated or unsaturated carbon chain or a 4- to 5-membered, saturated or unsaturated chain in which the members are carbon atoms and one or two nitrogen atoms or an oxygen atom. In one particular embodiment, R is a 5-membered, unsaturated chain in which the members are carbon atoms and one or two nitrogen atoms, and (Z)$_m$ includes an oxo group attached to a carbon atom not linked to another atom by an unsaturated bond.

Typical optional substituents (Z) of the heterocyclic ring X are halogen, C$_{1-4}$ alkyl, C$_{3-6}$ cycloalkyl, C$_{2-4}$ alkenyl, C$_{2-4}$ alkynyl, C$_{2-4}$ alkenyloxy, C$_{2-4}$ alkynyloxy, phenyl, benzyloxy, cyano, isocyano, isothiocyanato, nitro, oxo, NR$^1$R$^2$, NHCOR$^1$, NHCONR$^1$R$^2$, NHSO$_2$R$^1$, OR$^1$, OCOR$^1$, OSO$_2$R$^1$, SR$^1$, SOR$^1$, SO$_2$R$^1$, COR$^1$, CR$^1$=NOR$^2$, CO$_2$R$^1$, CONR$^1$R$^2$, CSNR$^1$R$^2$. When substituents are ortho to one another, they may join to form a 5- or 6-membered aliphatic or aromatic ring optionally containing one or more oxygen, sulphur or nitrogen atoms and optionally substituted with one or more of the substituents recited for X above. Suitably they join to form a benzene ring. Examples of the ring X where its substituents join to form a benzene ring are benzimidazole, benzotriazole and benzotriazinone. R$^1$ and R$^2$ are independently hydrogen, C$_{1-4}$ alkyl or phenyl. The aliphatic moieties of any of the substituents may themselves be substituted with one or more of halogen, cyano, OR$^1$ or OCOR$^1$ and the phenyl moieties of any of the substituents may themselves be substituted with one or more of halogen C$_{1-4}$ alkyl, C$_{1-4}$ alkoxy, nitro or cyano.

Alkyl groups contain from 1 to 4 carbon atoms and may be in the form of straight or branched chains. Examples are methyl, ethyl, iso-propyl, n-butyl and t-butyl. Substituted alkyl groups include C$_{1-4}$ haloalkyl groups and, in particular, trifluoromethyl groups. Cycloalkyl groups contain from 3 to 6 carbon atoms and include cyclopropyl and cyclohexyl.

Alkenyl and alkynyl groups contain from 2 to 4 carbon atoms and may be in the form of straight or branched chains. Examples are ethenyl, allyl, methylallyl and propargyl.

Halogen is typically fluorine, chlorine or bromine.

Aliphatic moieties which may be substituted include, in particular, C$_{1-4}$ alkyl groups.

In one aspect the invention provides a compound of the formula (I.1).

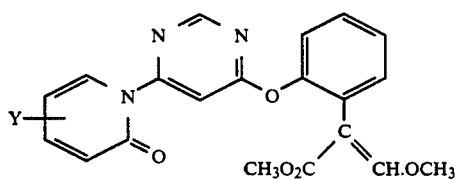

(I.1)

in which Y is H, $C_{1-4}$ alkyl (especially methyl) or trifluoromethyl.

The invention is illustrated by the compounds listed in Tables I to III which follow. Throughout these Tables the methyl 3-methoxypropenoate group has the (E)-configuration.

TABLE I

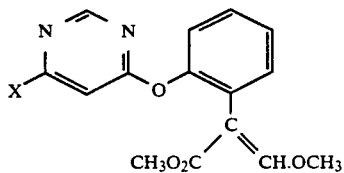

| Compound No. | X | M.pt. (°C.) | δ+ |
|---|---|---|---|
| 1 | aziridin-1-yl | | |
| 2 | azetidin-1-yl | | |
| 3 | pyrrolidin-1-yl | | |
| 4 | piperidin-1-yl | | |
| 5 | morpholin-4-yl | | |
| 6 | 2,6-dimethylmorpholin-4-yl | | |
| 7 | pyrrol-1-yl | | |
| 8 | imidazol-1-yl | Gum | 7.45 |

TABLE I-continued

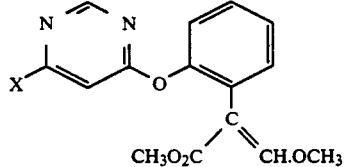

| Compound No. | X | M.pt. (°C.) | δ+ |
|---|---|---|---|
| 9 | pyrazol-1-yl | | |
| 10 | 1,2,4-triazol-1-yl | | |
| 11 | 1,2,3-triazol-1-yl | | |
| 12 | 1,2,3-triazol-2-yl | | |
| 13 | 2-oxopiperidin-1-yl | | |
| 14 | 4-oxopiperidin-1-yl | | |
| 15 | 3-oxopiperidin-1-yl | | |
| 16 | 2-oxo-1,2-dihydropyridin-1-yl | | |
| 17 | 3-methyl-2-oxo-1,2-dihydropyridin-1-yl | Glass | 7.47 |
| 18 | 4-trifluoromethyl-2-oxo-1,2-dihydropyridin-1-yl | 100–102 | 7.47 |

TABLE I-continued
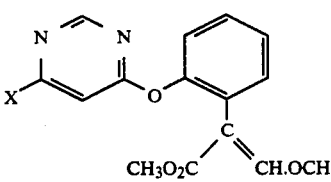
| Compound No. | X | M.pt. (°C.) | δ+ |
|---|---|---|---|
| 19 | 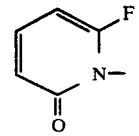 | | |
| 20 | 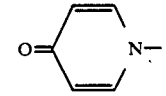 | | |
| 21 | 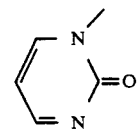 | | |
| 22 | 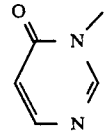 | | |
| 23 | 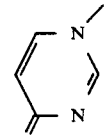 | | |
| 24 | 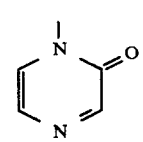 | | |
| 25 | 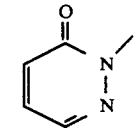 | | |
| 26 | 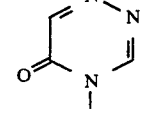 | | |
| 27 | 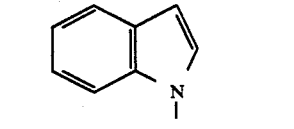 | | |
| 28 | 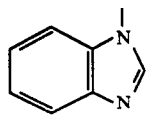 | | |
| 29 | 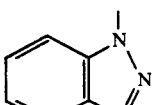 | | |
| 30 | 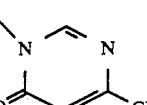 | 139–141° C. | 7.48 |
| 31 | 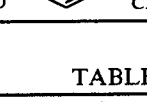 | 130–131° C. | 7.48 |
TABLE II
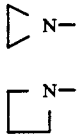
| Compound No. | X | M.pt. (°C.) | δ+ |
|---|---|---|---|
| 1 | 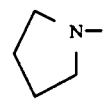 | | |
| 2 | 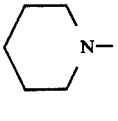 | | |
| 3 | 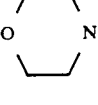 | | |
| 4 | | | |
| 5 | | | |

TABLE II-continued

[Structure: pyrimidine with X substituent, linked via O to phenyl ring bearing C(=CH.OCH3)(CO2CH3) group]

| Compound No. | X | M.pt. (°C.) | δ+ |
|---|---|---|---|
| 6 | 2,6-dimethylmorpholin-4-yl | | |
| 7 | pyrrol-1-yl | | |
| 8 | pyrazol-1-yl | | |
| 9 | pyrazol-1-yl | | |
| 10 | 1,2,4-triazol-1-yl | | |
| 11 | 1,2,4-triazol-4-yl | | |
| 12 | 1,2,3-triazol-1-yl (tetrazolyl) | | |
| 13 | 2-oxopiperidin-1-yl | | |
| 14 | 4-oxopiperidin-1-yl | | |
| 15 | 3-oxopiperidin-1-yl | | |
| 16 | 2-oxopyridin-1-yl | | |
| 17 | 3-methyl-2-oxopyridin-1-yl | | |
| 18 | 4-trifluoromethyl-2-oxopyridin-1-yl | | |
| 19 | 5-chloro-2-oxopyridin-1-yl | | |
| 20 | 6-fluoro-2-oxopyridin-1-yl | | |
| 21 | 4-oxopyridin-1-yl | | |
| 22 | 3-methyl-2-oxo-2,3-dihydropyrimidin-1-yl | | |
| 23 | 1-methyl-4-oxopyrimidin-1-yl | | |
| 24 | 1-methyl-6-oxopyrimidin-1-yl | | |

TABLE II-continued

Structure: X-substituted pyrimidine with O-phenyl linker bearing C(=CH.OCH₃)(CH₃O₂C) group

| Compound No. | X | M.pt. (°C.) | δ⁺ |
|---|---|---|---|
| 25 | 1-methyl-2-oxo-pyrazinyl | | |
| 26 | 3-oxo-pyridazinyl | | |
| 27 | 4-methyl-5-oxo-1,2,4-triazinyl | | |
| 28 | indol-1-yl | | |
| 29 | benzimidazol-1-yl | | |
| 30 | benzotriazol-1-yl | | |
| 31 | 1-methyl-6-oxo-4-(trifluoromethyl)pyrimidinyl | | |

TABLE III

Structure: 2-X-pyrimidin-4-yloxy phenyl with C(=CH.OCH₃)(CH₃O₂C) group

| Compound No. | X | M.pt. (°C.) | δ⁺ |
|---|---|---|---|
| 1 | aziridin-1-yl | | |
| 2 | azetidin-1-yl | | |
| 3 | pyrrolidin-1-yl | | |
| 4 | piperidin-1-yl | | |
| 5 | morpholin-4-yl | | |
| 6 | (2,6-dimethyl)morpholin-4-yl | | |
| 7 | 2,5-dihydropyrrol-1-yl | | |
| 8 | imidazol-1-yl | | |
| 9 | pyrazol-1-yl | | |
| 10 | 1,2,4-triazol-1-yl | | |
| 11 | 1,2,4-triazol-4-yl | | |
| 12 | 1,2,3-triazol-1-yl | | |

TABLE III-continued

[Structure: pyrimidine with X substituent, connected via O to phenyl ring bearing C(=CH.OCH3)CO2CH3 group]

| Compound No. | X | M.pt. (°C.) | δ+ |
|---|---|---|---|
| 13 | 2-oxo-piperidin-1-yl | | |
| 14 | 4-oxo-piperidin-1-yl | | |
| 15 | 3-oxo-piperidin-1-yl | | |
| 16 | 2-oxo-1,2-dihydropyridin-1-yl | | |
| 17 | 3-methyl-2-oxo-1,2-dihydropyridin-1-yl | | |
| 18 | 4-trifluoromethyl-2-oxo-1,2-dihydropyridin-1-yl | | |
| 19 | 5-chloro-2-oxo-1,2-dihydropyridin-1-yl | | |
| 20 | 6-fluoro-2-oxo-1,2-dihydropyridin-1-yl | | |
| 21 | 4-oxo-1,4-dihydropyridin-1-yl | | |
| 22 | 2-oxo-pyrimidin-1-yl | | |
| 23 | 4-oxo-pyrimidin-1-yl | | |
| 24 | 6-oxo-pyrimidin-1-yl | | |
| 25 | 2-oxo-pyrazin-1-yl | | |
| 26 | 2-methyl-3-oxo-pyridazin-2-yl | | |
| 27 | N-methyl-oxo-triazinyl | | |
| 28 | indol-1-yl | | |
| 29 | benzimidazol-1-yl | | |
| 30 | benzotriazol-1-yl | | |

TABLE III-continued

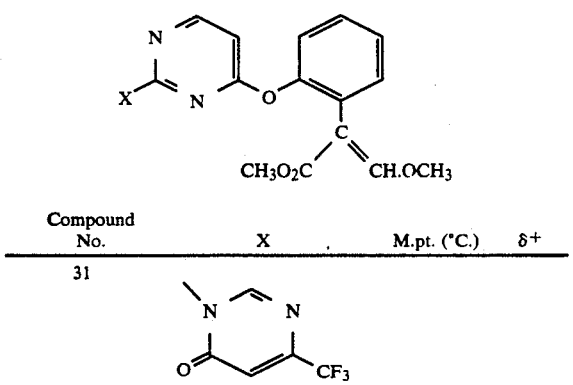

| Compound No. | X | M.pt. (°C.) | δ+ |
|---|---|---|---|
| 31 | (structure with N=CH-N, O, CF₃) | | |

+Chemical shift of singlet from olefinic proton on β-methoxypropenoate group (ppm from tetramethylsilane).

The compounds of the invention of formula (I) [equivalent to (IA) when W is the group $CH_3O_2C.C=CH.OCH_3$] can be prepared by the steps shown in Schemes I and II. In these Schemes the terms K, L, and M are as defined above; X' is either X, or is a group which can be converted into X by methods described in the chemical literature, wherein X is as described above; W is $CH_3O_2C.C=CH.OCH_3$ or a group that can be transformed into $CH_3O_2C.C=CH.OCH_3$ using methods previously described such as in EP-A-0242081; $Z^1$ and $Z^2$ are leaving groups (such as halogen or $CH_3SO_2-$); and T is hydrogen or a metal (such as sodium). The reactions shown in Schemes I and II are performed either in a suitable solvent or without a solvent, and at a suitable temperature.

Thus compounds of the invention of formula (IA) can be prepared by treatment of substituted pyrimidines of general formula (III) with phenols of formula (II) (wherein W is as defined above and T is hydrogen) in the presence of a base (such as potassium carbonate) (Scheme I).

Alternatively, compounds of formula (IA) can be prepared by treatment of substituted pyrimidines of general formula (III) with phenolate salts of formula (II) (wherein W is as defined above and T is a metal, such as sodium) (Scheme I).

Scheme I

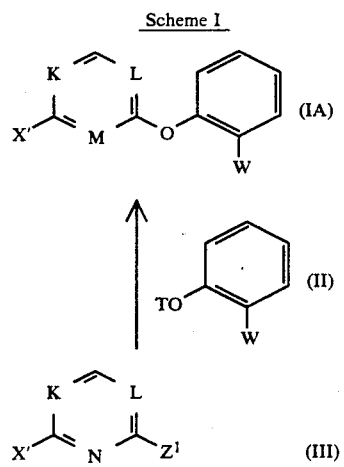

Alternatively, the compounds of the invention of formula (I) (equivalent to (IA) when W is the group $CH_3O_2C.C=CH.OCH_3$) can be prepared by the steps shown in Scheme II.

Thus compounds of the invention of formula (IA) can be prepared by treatment of substituted pyrimidines of general formula (IV) with heterocycles of general formula (V) (wherein X' is as defined above and T is hydrogen) in the presence of a base (such as potassium carbonate).

Alternatively, compounds of the invention of formula (IA) can be prepared by treatment of substituted pyrimidines of general formula (IV) with salts of formula (V) (wherein X' is as defined above and T is a metal, such as sodium).

Substituted pyrimidines of general formula (IV) can be prepared by treatment of pyrimidines of general formula (VI) with phenols of general formula (II) (wherein W is as defined above and T is hydrogen) in the presence of a base (such as potassium carbonate).

Scheme II

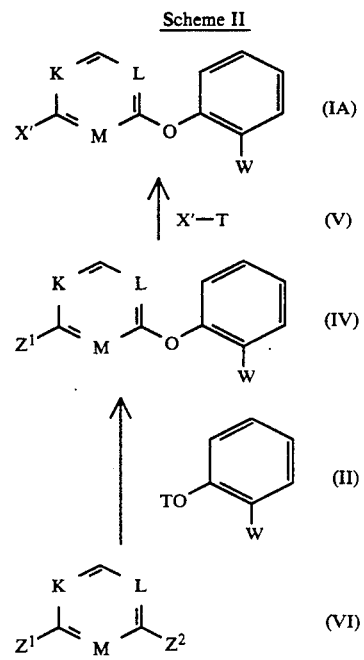

Alternatively, substituted pyrimidines of general formula (IV) can be prepared by treatment of pyrimidines of general formula (VI) with phenolate salts of general formula (II) (wherein W is as defined above and T is a metal, such as sodium).

The last stage of the synthesis of the compounds of the invention may therefore be one of the following:

(i) construction of the group $CH_3O_2C.C=CH.OCH_3$ [in which case the group W in the compounds (II), (IV) and (IA) represents an appropriate precursor to the group $CH_3O_2C.C=CH.OCH_3$ during the coupling reactions shown in Schemes I and II]; or (ii) the coupling reaction shown in Scheme I or the second coupling reaction shown in Scheme II [in which case the group W in the intermediates (II) or (IV) represents the group $CH_3O_2C.C=CH.OCH_3$]; or (iii) construction of the group X from the group X' (this could be the modification of a substituent on the group X').

Pyrimidines of formulae (III) and (VI) and heterocycles of formula (V) can be prepared by standard methods described in the chemical literature. Compounds of formula (II) can either be prepared by standard methods described in the chemical literature, or when W is $CH_3O_2C.C=CH.OCH_3$, can be prepared by methods described in EP-A-0242081.

In a further aspect, the invention provides processes as herein described for preparing the compounds of the invention.

The compounds of the invention are active fungicides and may be used to control one or more of the following pathogens:

The compounds are active fungicides and may be used to control one or more of the following pathogens: *Pyricularia oryzae* on rice. *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines. Helminthosporium spp., Rhynchosporium spp., Septoria spp., Pyrenophora spp., *Pseudocercosporella herpotrichoides* and *Gaeumannomyces graminis* on cereals. *Cercospora arachidicola* and *Cercosporidium personata* on peanuts and other Cercospora species on other hosts, for example, sugar beet, bananas, soya beans and rice. *Botrytis cinerea* (grey mould) on tomatoes, strawberries, vegetables, vines and other hosts. Alternaria spp. on vegetables (e.g. cucumber), oil-seed rape, apples, tomatoes and other hosts. *Venturia inaequalis* (scab) on apples. *Plasmopara viticola* on vines. Other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits. *Phytophthora infestans* on potatoes and tomatoes and other Phytophthora spp. on vegetables, strawberries, avocado, pepper, ornamentals, tobacco, cocoa and other hosts. *Thanatephorus cucumeris* on rice and other Phizoctonia species on various hosts such as wheat and barley, vegetables, cotton and turf.

Some of the compounds shown a broad range of activities against fungi in vitro. They may also have activity against various post-harvest diseases of fruit (e.g. *Penicillium digitatum* and italicum and *Trichoderma viride* on oranges, *Gloeosporium musarum* on bananas and *Botrytis cinerea* on grapes).

Further, some of the compounds may be active as seed dressings against pathogens including Fusarium spp., Septoria spp., Tilletia spp., (bunt, a seed-borne disease of wheat), Ustilago spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H-1,2,4-triazol-1-yl-methyl)butyronitrile, (Z)-N-but-2-enyloxymethyl-2-chloro-2',6'-diethylacetanilide, 1-(2-cyano-2-methoxyiminoacetyl)-3-ethyl urea, 1-[(2RS,4RS;2RS,4RS)-4-bromo-2-(2,4-dichlorophenyl)tetrahydrofurfuryl]-1H-1,2,4-triazole, 3-(2,4-dichlorophenyl)-2-(1H-1,2,4-triazol-1-yl)quinazolin-4(3H)-one, 3-chloro-4-[4-methyl-2-(1H-1,2,4-triazol-1-methyl)-1,3-dioxolan-2-yl]phenyl-4-chlorophenyl ether, 4-bromo-2-cyano-N,N-dimethyl-6-trifluoromethylbenzimidazole-1-sulphonamide, 5-ethyl-5,8-dihydro-8-oxo(1,3)-dioxolo(4,5-g)quinoline-7-carboxylic acid, α-[N-(3-chloro-2,6-xylyl)-2-methoxyacetamido]-γ-butyrolactone, aldimorph, anilazine, benalaxyl, benomyl, biloxazol, binapacryl, bitertanol, blasticidin S, bupirimate, buthiobate, captafol, captan, carbendazim, carboxin, chlorbenz-thiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneamino-oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, N-(4-methyl-6-prop-1-ynylpyrimidin-2-yl)aniline, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, SSF-109, streptomycin, sulphur, tebuconazole, techlofthalam, tecnazene, tetra-conazole, thiabendazole, thicyofen, thiophanate-methyl, thiram, tolclofos-methyl, triacetate salt of 1,1'-iminodi(octa-methylene)diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention. In the Examples, the term 'ether' refers to diethyl ether, anhydrous magnesium sulphate was used to dry solutions, and solutions were concentrated under reduced pressure. Reactions involving air- or water-sensitive intermediates were performed under an atmosphere of nitrogen and solvents were dried before use, where appropriate. Unless otherwise stated, chromatography was performed on a column of silica gel as the stationary phase. NMR data are selective; no attempt is made to list every absorption in all cases. $^1$H NMR spectra were recorded using $CDCl_3$-solutions. The following abbreviations are used:

DMF=N,N-dimethylformamide
NMR=nuclear magnetic resonance
IR=infrared
s=singlet
d=doublet
m=multiplet
t=triplet
mp=melting point
ppm=parts per million.

EXAMPLE 1

This Example illustrates the preparation of (E)-methyl 2-[2-(6-(3-methylpyridin-2-onyl)-pyrimidin-4-yloxy)phenyl]-3-methoxypropenoate (Compound No. 17 of Table I).

To a solution of 4,6-dichloropyrimidine (0.76 g, 5.10 mmol) in dry DMF (4 ml) at 0° C. was added anhydrous potassium carbonate (0.70 g, 5.10 mmol). A solution of (E)-methyl 2-(2-hydroxyphenyl)-3-methoxypropenoate (0.53 g, 2.55 mmol) in dry DMF (2 ml) was then added dropwise with stirring. After the addition was complete, the reaction mixture was allowed to warm to room temperature and stirring continued over the weekend. The reaction mixture was then diluted with water (15 ml) and extracted with ether (3×20 ml). The combined ether extracts were washed with brine and dried. Evaporation afforded a brown liquid (1.10 g) which was chromatographed (eluent ether:n-hexane, 3:2) to give (E)-methyl 2-[2-(6-chloropyrimidin-4-yloxy)phenyl]-3-methoxy-propenoate as a thick, pale yellow oil (0.58, 71%) which crystallised on standing.

Recrystallisation from ether/dichloromethane(-trace)/n-hexane at −78° C. gave the product as a white powder (0.25 g), mp 94°-5° C. In a separate preparation, 15 g of product was obtained from 4,5-dichloropyrimidine (15.90 g), (E)-methyl 2-(2-hydroxyphenyl)-3-methoxy-propenoate (14.80 g) and anhydrous potassium carbonate (19.64 g).

To a suspension of (E)-Methyl 2-[2-(6-chloropyrimidin-4-yloxy)phenyl]-3-methoxypropenoate (0.50 g, 1.56 mmol) in dry toluene (25 ml) were added 3-methyl-2-pyridone (0.17 g, 1.72 mmol) and silver carbonate (0.47 g, 1.72 mmol). The mixture was refluxed overnight and then further amounts of 3-methyl-2-pyridone (0.08 g) and silver carbonate (0.23 g) were added. The resulting mixture was heated at reflux overnight, cooled and filtered through a plug of celite. The celite was washed through with toluene (2×20 ml) and the combined solutions evaporated to give a brown oil (0.75 g). Chromatography on silicagel (eluent ethyl acetate:n-hexane, 3:1) afforded the title compound as a pale yellow foam which set to a glass (0.19 g, 31%); IR max. 1664 cm$^{-1}$, $^1$H NMR ($CDCl_3$) δ2.19(3H,s); 3.62(3H,s); 3.73(3H,s); 6.24(1H,t); 7.20-7.51(5H,m); 7.47(1H,s); 7.77(1H,s); 7.99(1H,d); 8.73(1H,s) ppm.

Mass spectrum m/e 393 (M+).

EXAMPLE 2

This Example illustrates the preparation of (E)-methyl 2-[2-(6-(benztriazol-1-yl)pyrimidin-4-yloxy)-phenyl]-3-methoxypropenoate (Compound No. 30 of Table I).

A mixture containing benzotriazole (0.262 g, 2.2 mmol) and anhydrous potassium carbonate (0.30 g, 2.2 mmol) in dry DMF (5 ml) was heated at 100° C. for one hour under an atmosphere of nitrogen. The resulting grey mixture was cooled to −40° C. and a solution of (E)-methyl 2-[2-(6-chloropyrimidin-4-yloxy)phenyl]-3-methoxypropenoate (0.641 g, 2 mmol) in dry DMF (5 ml) was added drop-wise over ten minutes. The reaction mixture was stirred for a further ten minutes, allowed to warm to room temperature and then stirred for 4¼ hours. The reaction mixture was filtered and the filtrate diluted with water and extracted with ether (×4). The combined ether extracts were washed with water, dried and evaporated to give an orange residue (0.40 g). Chromatography on silicagel (eluent acetone:hexane, 1:4) afforded the title compound as a yellow solid (0.03 g); m.p. 139°-141° C.; IR max. 1709, 1632 cm$^{-1}$; $^1$H NMR ($CDCl_3$) δ3.61(3H,s); 3.75(3H,s); 7.24-7.28(1H,m); 7.31-7.53(4H,m); 7.48(1H,s); 7.62-7.69(2H,m); 8.12-8.15(1H,d); 8.65-8.68(1H,d); 8.82(1H,s) ppm.

EXAMPLE 3

This Example illustrates the preparation of (E)-methyl 2-[2-(6-(imidazol-1-yl)pyrimidin-4-yloxy)-phenyl]-3-methoxypropenoate (Compound No. 8 of Table I).

To a stirred suspension of sodium hydride (0.65 g, 55% dispersion in oil, pre-washed with petrol) in dry DMF (5 ml) at 10°-15° C. under nitrogen, was added a solution of imidazole (1.02 g, 15 mmol) over five minutes. The reaction mixture effervesced and an exotherm took place. After stirring for 1½ hours at room temperature, the cloudy solution was added drop-wise over one hour to a solution of 4,6-dichloropyrimidine in dry DMF (10 ml) at 0° C. for one hour, added to water and then extracted with ether (×3). The combined ether extracts were washed with dilute sodium hydroxide solution and water (×3) and then dried. Concentration under reduced pressure gave 4-chloro-6-(imidazol-1-yl)pyrimidine as a pale yellow solid (1.00 g); m.p. 122°-4° C., which was used without further purification.

A solution of 4-chloro-6-(imidazol-1-yl)pyrimidine (0.54 g, 3 mmol) in dry DMF (5 ml) was added drop-wise over five minutes to sodium thiomethoxide (0.23 g, 3.15 mmol) in dry DMF (5 ml) at 0° C. under nitrogen. After stirring at 0° C. for 45 minutes, the reaction mixture was allowed to warm to room temperature. After two hours, the reaction mixture was poured into water and extracted with ether (×3). The combined ether extracts were washed with water, dried and evaporated to give a pale yellow solid (0.30 g). Chromatography on silicagel (eluent ether) afforded 4-(imidazol-1-yl)-6-thiomethoxypyrimidine (0.08 g) as a white solid, m.p. 123°-5° C. A second fraction (0.14 g) containing 88% of the desired product as a white solid was also isolated. Treatment of this material (0.14 g) with finely ground potassium permanganate (0.14 g) in aqueous acetic acid (7.5 ml) at room temperature for two hours afforded a brown solution which was left to stand overnight. Sulphur dioxide was passed through the solution until decolourisation had taken place and the resulting solution was extracted with ethyl acetate (×2). The combined organic layers dried and evaporated to give a yellow gum (0.10 g). The gum was redissolved in dichloromethane, washed with sodium bicarbonate solution and water (×2) and then dried and concentrated to afford crude 4-(imidazol-1-yl)-6-methanesulphonylpyrimidine (0.06 g), which was used without further purification.

A solution of crude 4-(imidazol-1-yl)-6-methanesulphonylpyrimidine (0.06 g) in dry DMF (2 ml) was added over one minute to a stirred suspension of (E)-methyl 2-(2-hydroxyphenyl)-3-methoxypropenoate (0.056 g) and potassium carbonate (0.037 g) in DMF (3 ml) at 5° C. The reaction mixture was stirred at 5° C. for fifteen minutes and then allowed to warm to room temperature. After stirring overnight, the reaction mixture was poured into water and extracted with ether (×4). The combined extracts were washed with dilute sodium hydroxide solution (×2) and water (×3) and then dried. Evaporation gave a colourless gum (0.05 g). Chromatography on silicagel (eluent ethyl acetate) afforded the title compound as a colourless gum (0.03 g); IR max. 1705, 1620 cm$^{-1}$.

$^1$H NMR (CDCl$_3$) δ3.59(3H,s); 4.74(3H,s); 6.66(1H,s); 7.19-7.46(5H,m); 7.45(1H,s); 7.58(1H,m); 8.40(1H,s); 8.66(1H,s) ppm.

EXAMPLE 4

This Example illustrates the preparation of (E)-methyl 2-[2-(6-(1,2,4-triazol-1-yl)pyrimidin-4-yloxy)phenyl]-3-methoxypropenoate (Compound No. 10 of Table I).

To a stirred suspension of sodium hydride (0.87 g, 55% dispersion in oil, pre-washed with petrol) in dry DMF (5 ml) under nitrogen at 10°-18° C. was added drop-wise a solution of 1,2,4-triazole (1.38, 20 mmol) in dry DMF (10 ml) (effervescence). The reaction mixture was stirred at room temperature for one hour, cooled to 0°-4° C. and then a solution of 4,6-dichloropyrimidine (2.98 g, 20 mmol) in dry DMF (10 ml) added drop-wise over 45 minutes. The resulting reddish solution was stirred for 90 minutes at 0° C. and then poured into water. A buff-coloured precipitate (0.88 g) was formed, which was isolated by filtration and characterised as 4,6-di(1,2,4-triazol-1-yl)pyrimidine, m.p. 204°-208° C. The aqueous filtrate was extracted with ether (×3) and the combined ether extracts washed with brine and water (×2). The pale yellow solution was dried and concentrated under reduced pressure to give a pale cream-coloured solid (1.50 g), which was recrystallised from dichloromethane-petrol to afford 4-chloro-6-(1,2,4-triazol-1-yl)pyrimidine (1.08 g) as an off-white solid, m.p. 93°-7° C.

To a stirred suspension of sodium thiomethoxide (0.39 g, 1.05 equ.) in dry DMF (5 ml) under nitrogen at 0° C. was added drop-wise over 15 minutes a solution containing 4-chloro-6-(1,2,4-triazol-1-yl) in dry DMF (10 ml). After stirring at 0° C. for 90 minutes, the reaction mixture was poured into water and extracted with ethyl acetate (×3). The combined organic extracts were washed with brine (×2), dried and evaporated to give a yellow solid (0.60 g). Chromatography on silicagel (eluent ether) gave 4-thiomethyl-6-(1,2,4-triazol-1-yl)pyrimidine (0.20 g) as a white solid (85% pure by g.c) which was used in the next stage without further purification.

The product (0.20 g) was dissolved in glacial acetic acid (3.5 ml) at 10°-15° C. and a solution of finely ground potassium permanganate (0.20 g) in water (7 ml) added drop-wise over 15 minutes. The dark brown reaction mixture was stirred overnight at room temperature and then sulphur dioxide was passed through until decolourisation had taken place. The aqueous solution was extracted with ethyl acetate and the combined organic layers washed with aqueous sodium bicarbonate solution (×4) and water and then dried. The solvent was removed under reduced pressure to give a white gum (0.12 g). Trituration with ether afforded 4-(methanesulphonyl)-6-(1,2,4-triazol-1-yl)pyrimidine (0.052 g) as a solid.

To a stirred suspension containing anhydrous potassium carbonate (28 mg) and (E)-methyl 2-(2'-hydroxyphenyl)-3-methoxypropenoate (43 mg) in dry DMF (3 ml) at 0° C. was added a solution of 4-(methanesulphonyl)-6-(1,2,4-triazol-1-yl)pyrimidine (46 mg) in dry DMF (2 ml). The reaction mixture was stirred at 0°-2° C. for 20 minutes and then allowed to warm to room temperature. After two hours, the reaction mixture was poured into water and extracted with ether (×4). The combined extracts were washed with dilute sodium hydroxide solution (×2) followed by water (×3) and then dried. Evaporation under reduced pressure gave a white foam (0.05 g) which was recrystallised from dichloromethane-petrol to afford the title compound (37 mg) as white solid; m.p. 127°-8° C., IR max. 1692, 1625 cm$^{-1}$;

$^1$H NMR (CDCl$_3$) δ3.60(3H,s); 3.75(3H,s); 7.20-7.44(5H,m); 7.46(1H,s); 8.12(1H,s); 8.65(1H,s); 9.20(1H,s) ppm.

EXAMPLE 5

This Example illustrates the preparation of (E)-methyl 2-[2-(6-(4-trifluoromethyl-6-oxopyrimidin-1- yl)pyrimidin-4-yloxy)phenyl]-3-methoxypropenoate (compound No. 31 of Table I).

To a stirred suspension of sodium hydride (0.14 g, 3.2 mmol, 55% dispersion in oil, pre-washed with n-hexane) in dry DMF (10 ml) was added drop-wise a solution of 4-hydroxy-6-trifluoromethylpyrimidine (0.50 g, 3.05 mmol) in dry DMF (6 ml). The mixture was stirred for a further one hour until all evolution of hydrogen had ceased. To the resulting cloudy suspension was added a solution of (E)-methyl 2-[2-(6-chloropyrimidin-4-yloxy)phenyl]-3-methoxypropenoate (0.98 g, 3.05 mmol) in dry DMF (9 ml). After stirring at room temperature for one hour, a catalytic amount of copper(I) chloride was added and the reaction mixture heated over the weekend at 110° C. The brown reaction mixture was cooled, diluted with dichloromethane (30 ml) and filtered. The filter pad was washed with dichloromethane (2×15 ml) and the combined filtrate washed with water (2×35 ml). An emulsion formed during each wash which could be broken up by filtration. The dichloromethane layer was separated, treated with charcoal, dried and evaporated to give a dark brown oil (0.98 g). Chromatography on silica gel (eluent ethylacetate-n-hexane, 5:2) gave the title compound as a gum which crystallised from ether-hexane as a cream-coloured solid (0.13 g, 9.5%); m.pt. 130°–1° C., infrared maxima 1718, 1700, 1629 cm$^{-1}$.

$^1$H NMR (CDCl$_3$) δ3.62(3H,s); 3.76(3H,s); 6.92(1H,s); 7.19–7.52(4H,m); 7.48(1H,s); 7.61(1H,s); 7.8(1H,s); 9.02(1H,s) ppm.

The following are examples of compositions suitable for agricultural and horticultural proposes which can be formulated from the compounds of the invention. Such compositions form another aspect of the invention. Percentages are by weight.

EXAMPLE 6

An emulsifiable concentrate is made up by mixing and stirring the ingredients until all are dissolved.

| | |
|---|---|
| Compound No. 18 of Table I | 10% |
| Benzyl alcohol | 30% |
| Calcium dodecylbenzenesulfphonate | 5% |
| Nonylphenolethoxylate (13 mole ethylene oxide) | 10% |
| Alkyl benzenes | 45% |

EXAMPLE 7

The active ingredient is dissolved in methylene dichloride and the resultant liquid sprayed on to the granules of attapulgite clay. The solvent is then allowed to evaporate to produce a granular composition.

| | |
|---|---|
| Compound No. 18 of Table I | 5% |
| Attapulgite granules | 95% |

EXAMPLE 8

A composition suitable for use as a seed dressing is prepared by grinding and mixing the three ingredients.

| | |
|---|---|
| Compound No. 18 of Table I | 50% |
| Mineral oil | 2% |
| China clay | 48% |

EXAMPLE 9

A dustable powder is prepared by grinding and mixing the active ingredient with talc.

| | |
|---|---|
| Compound No. 18 of Table I | 5% |
| Talc | 95% |

EXAMPLE 10

A suspension concentrate is prepared by ball milling the ingredients to form an aqueous suspension of the ground mixture with water.

| | |
|---|---|
| Compound No. 18 of Table I | 40% |
| Soidum lignosulphonate | 10% |
| Bentonite clay | 1% |
| Water | 49% |

This formulation can be used as a spray by diluting into water or applied directly to seed.

EXAMPLE 11

A wettable powder formulation is made by mixing together and grinding the ingredients until all are throughly mixed.

| | |
|---|---|
| Compound No. 18 of Table I | 25% |
| Sodium lauryl sulphate | 2% |
| Sodium lignosulphonate | 5% |
| Silica | 25% |
| China clay | 43% |

EXAMPLE 12

The compounds were tested against a variety of foliar fungal diseases of plants. The technique employed was as follows.

The plants were grown in John Innes Potting Compost (no 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. Alternatively, the compounds were applied as a foliar spray only at a concentration of 10 ppm. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace-5% of disease on untreated plants
2 = 6-25% of disease on untreated plants
1 = 26-59% of disease on untreated plants
0 = 60-100% of disease on untreated plants.
The results are shown in Table IV.

TABLE IV

| COMPOUND NO | TABLE NO | PUCCINIA RECONDITA (WHEAT) | ERYSIPHE GRAMINIS (BARLEY) | VENTURIA INAEQUALIS (APPLE) | PYRICULARIA ORYZAE (RICE) |
|---|---|---|---|---|---|
| 8 | I | 3$^a$ | 0$^a$ | 0$^a$ | 0$^a$ |
| 10 | I | 0$^a$ | 0$^a$ | 0$^a$ | 0$^a$ |
| 17 | I | 4 | 4 | 4 | 4 |
| 18 | I | — | 4 | 4 | 4 |
| 30 | I | 4$^a$ | 4$^a$ | 4$^a$ | 3$^a$ |
| 31 | I | 0$^a$ | — | 3$^a$ | — |

| COMPOUND NO | TABLE NO | CERCOSPORA ARACHIDICOLA (PEANUT) | PLASMOPARA VITICOLA (VINE) | PHYTOPHTHORA INFESTANS LYCOPERSICI (TOMATO) |
|---|---|---|---|---|
| 8 | I | 2$^a$ | 0$^a$ | 0$^a$ |
| 10 | I | 2$^a$ | 0$^a$ | 0$^a$ |
| 17 | I | 4 | 4 | 0 |
| 18 | I | — | 4 | 0 |
| 30 | I | — | 4$^a$ | 4$^a$ |
| 31 | I | — | 0$^a$ | 0$^a$ |

$^a$ = 10 ppm foliar application only
— = no result

We claim:

1. A compound having the formula (I):

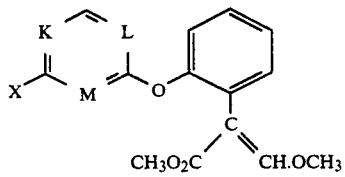

in which any two of K, L and M are nitrogen and the other is CH; and X is an optionally substituted 6-membered heterocyclic ring containing at least one trivalent nitrogen atom by which it is attached to the central pyrimidine ring; the heterocyclic ring being selected from the group consisting of pyrimidinone, pyrazinone, pyridazinone, 1,2,4-triazinone, 1,3,5-triazinone and morpholine and the optional substituents being selected from the group consisting of halogen, $C_{1-4}$ alkyl, $C_{3-6}$ cycloalkyl, $C_{2-4}$ alkenyl, $C_{2-4}$ alkynyl, $C_{2-4}$ alkenyloxy, $C_{2-4}$ alkynyloxy, phenyl, benzyloxy, cyano, isocyano, isothiocyanato, nitro, oxo, $NR^1R^2$, $NHCOR^1$, $NHCONR^1R^2$, $NHSO_2R^1$, $OR^1$, $OCOR^1$, $OS_2R^1$, $SR^1$, $SOR^1$, $SO_2R^1$, $COR^1$, $CR^1=NOR^2$, $CO_2R^1$, $CONR^1R^2$ and $CSNR^1R^2$, wherein $R^1$ and $R^2$ are independently hydrogen, $C_{1-4}$ alkyl or phenyl, and wherein the aliphatic moieties of any of the substituents are substituted with one or more of halogen, cyano, $OR^1$ or $OCOR^1$ and the phenyl moieties of any of the substituents being substituted with one or more of halogen, $C_{1-4}$ alkyl, $C_{1-4}$ alkoxy, nitro or cyano; or any two substitutents, when ortho to one another, join to form a benzene ring which is optionally substituted with one or more of the substituents recited above for the optionally substituted heterocyclic ring.

2. A compound according to claim 1 in which K and L are nitrogen, M is CH, and X is an optionally substituted heterocyclic ring selected from the group consisting of pyrimidinone, pyrazinone, pyridazinone, 1,2,4-triazinone and 1,3,5-triazinone.

3. A compound according to claim 2 in which X is an optionally substituted pyrimidinone.

4. A compound according to claim 2 in which X is an optionally substituted pyrazinone.

5. A compound according to claim 2 in which X is an optionally substituted pyridazinone.

6. A compound according to claim 2 in which X is an optionally substituted 1,2,4-triazinone.

7. A compound according to claim 2 in which X is an optionally substituted 1,3,5-triazinone.

8. A compound according to claim 6 (E)-methyl 2-[-(6-(4-trifluoromethyl-6-oxopyrimidin-1-yl)pyrimidin-4-yloxy)phenyl]-3-methoxy-propenoate.

9. A fungicidal composition comprising a fungicidally effective amount of a compound according to claim 1 and a fungicidally acceptable carrier or diluent therefor.

10. A method of combating fungi which comprises applying to plants, to the seeds of plants or to the locus of the plants or seeds, a compound according to claim 1 or a composition according to claim 9.

* * * * *